(12) United States Patent
Konno et al.

(10) Patent No.: US 10,925,507 B2
(45) Date of Patent: Feb. 23, 2021

(54) PHYSIOLOGICAL INFORMATION DETECTION SENSOR

(71) Applicant: NIHON KOHDEN CORPORATION, Tokyo (JP)

(72) Inventors: Norihito Konno, Tokyo (JP); Minori Hosoi, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 301 days.

(21) Appl. No.: 15/949,603

(22) Filed: Apr. 10, 2018

(65) Prior Publication Data
US 2018/0303371 A1   Oct. 25, 2018

(30) Foreign Application Priority Data

Apr. 21, 2017   (JP) .............................. JP2017-084500

(51) Int. Cl.
*A61B 5/0428*   (2006.01)
*H05K 1/14*   (2006.01)
(Continued)

(52) U.S. Cl.
CPC ........ *A61B 5/04282* (2013.01); *A61N 1/3925* (2013.01); *H05K 1/0256* (2013.01); *H05K 1/147* (2013.01); *A61B 5/0402* (2013.01); *A61B 2562/164* (2013.01); *A61B 2562/182* (2013.01); *H05K 1/0257* (2013.01); *H05K 1/181* (2013.01); *H05K 2201/042* (2013.01); *H05K 2201/056* (2013.01); *H05K 2201/10022* (2013.01); *H05K 2201/10151* (2013.01)

(58) Field of Classification Search
CPC .............. A61B 5/04282; A61B 5/0402; A61B 2562/164; A61B 2562/182; A61N 1/3925; H05K 1/0256; H05K 1/147; H05K 1/0257; H05K 1/181; H05K 2201/042; H05K 2201/056; H05K 2201/10022; H05K 2201/10151
See application file for complete search history.

(56) References Cited

U.S. PATENT DOCUMENTS 5,341,806 A * 8/1994 Gadsby .............. A61B 5/04085
                                                            600/393
2019/0015008 A1 * 1/2019 Alizadeh .............. A61B 5/6832

FOREIGN PATENT DOCUMENTS

JP       2014-068718       4/2014

* cited by examiner

*Primary Examiner* — Lindsey G Wehrheim
(74) *Attorney, Agent, or Firm* — Dorsey & Whitney LLP

(57) ABSTRACT

Provided is a physiological information detection sensor capable of implementing miniaturization by substantially securing a creepage distance and an air distance (e.g., implementing defibrillation protection).
The physiological information detection sensor includes: a plurality of first substrates arranged in multiple tiers; a second substrate; a first connecting portion that electrically connects adjacent first substrates to each other among the plurality of first substrates; and an insulating member. Each of the plurality of first substrates has a defibrillation protection resistor mounted thereon and electrically connected to a physiological information detection unit. The second substrate has a circuit mounted thereon to process physiological information input from the physiological information detection unit via the defibrillation protection resistor. The insulating member is disposed between adjacent first substrates among the plurality of first substrates.

19 Claims, 9 Drawing Sheets

(51) Int. Cl.
  *A61N 1/39* (2006.01)
  *H05K 1/02* (2006.01)
  *H05K 1/18* (2006.01)
  *A61B 5/0402* (2006.01)

FIG. 7
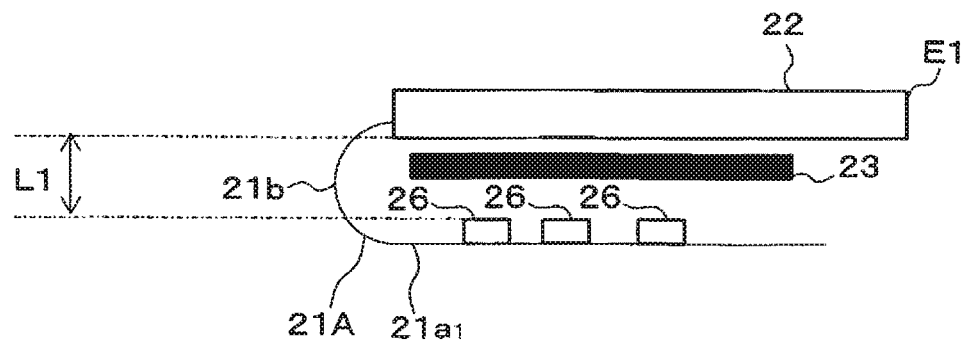
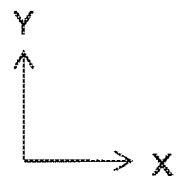
FIG. 8
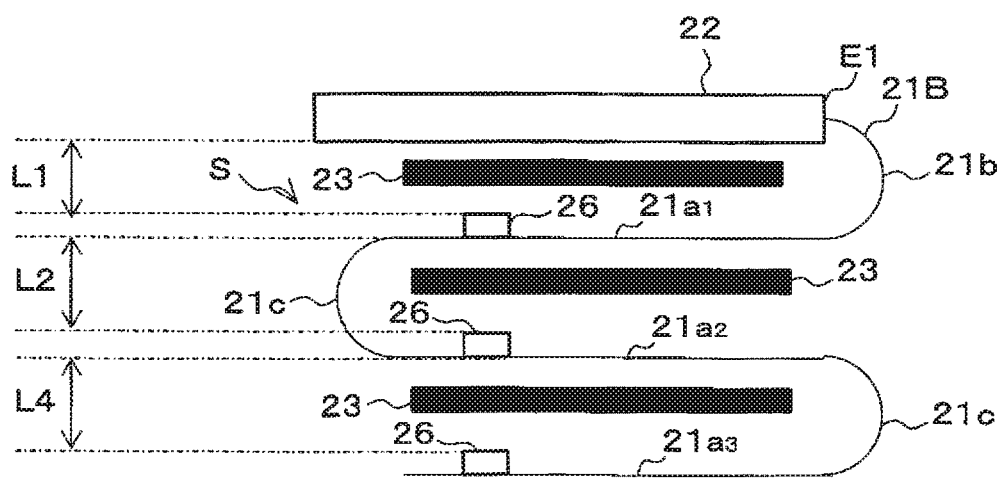
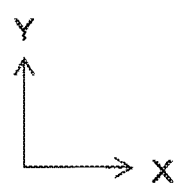

PHYSIOLOGICAL INFORMATION DETECTION SENSOR

CROSS-REFERENCE TO RELATED APPLICATION

This application claims priority to and the benefit under 35 U.S.C. § 119(a) of the earlier filing date of Japanese Patent Application No. 2017-84500 filed Apr. 21, 2017, the disclosure of which is hereby incorporated by reference, in its entirety, for any purpose.

BACKGROUND

1. Field

The present disclosure relates to a physiological information detection sensor.

2. Description of Related Art

In the related field of medical devices, a physiological information detection sensor using a defibrillation protection resistor for defibrillation protection (medical telemeter) has been known (see, e.g., JP-A-2014-068718).

SUMMARY

In general, however, in the case of mounting a defibrillation protection resistor for defibrillation protection in a physiological information detection sensor, from a viewpoint of protecting sensor or the like a creepage distance (e.g., 4 mm) and an air distance (e.g., 4 mm) may be utilized. Therefore, there may be a problem in that it is difficult to miniaturize the physiological information detection sensor.

The present disclosure has been made in consideration of the above circumstances, and an object thereof is to provide a physiological information detection sensor capable of implementing miniatudefibrillation protection resistorrization while substantially ensuring a creepage distance and an air distance (e.g., implementing defibrillation protection).

BRIEF DESCRIPTION OF THE DRAWINGS

FIG. 3 is a hardware configuration diagram of the physiological information detection sensor 20 and the like.

FIG. 7 is a view for explaining a modification of the flexible substrate 21.

FIG. 8 is a view for explaining another modification of the flexible substrate 21.

DETAILED DESCRIPTION

Figure 1:
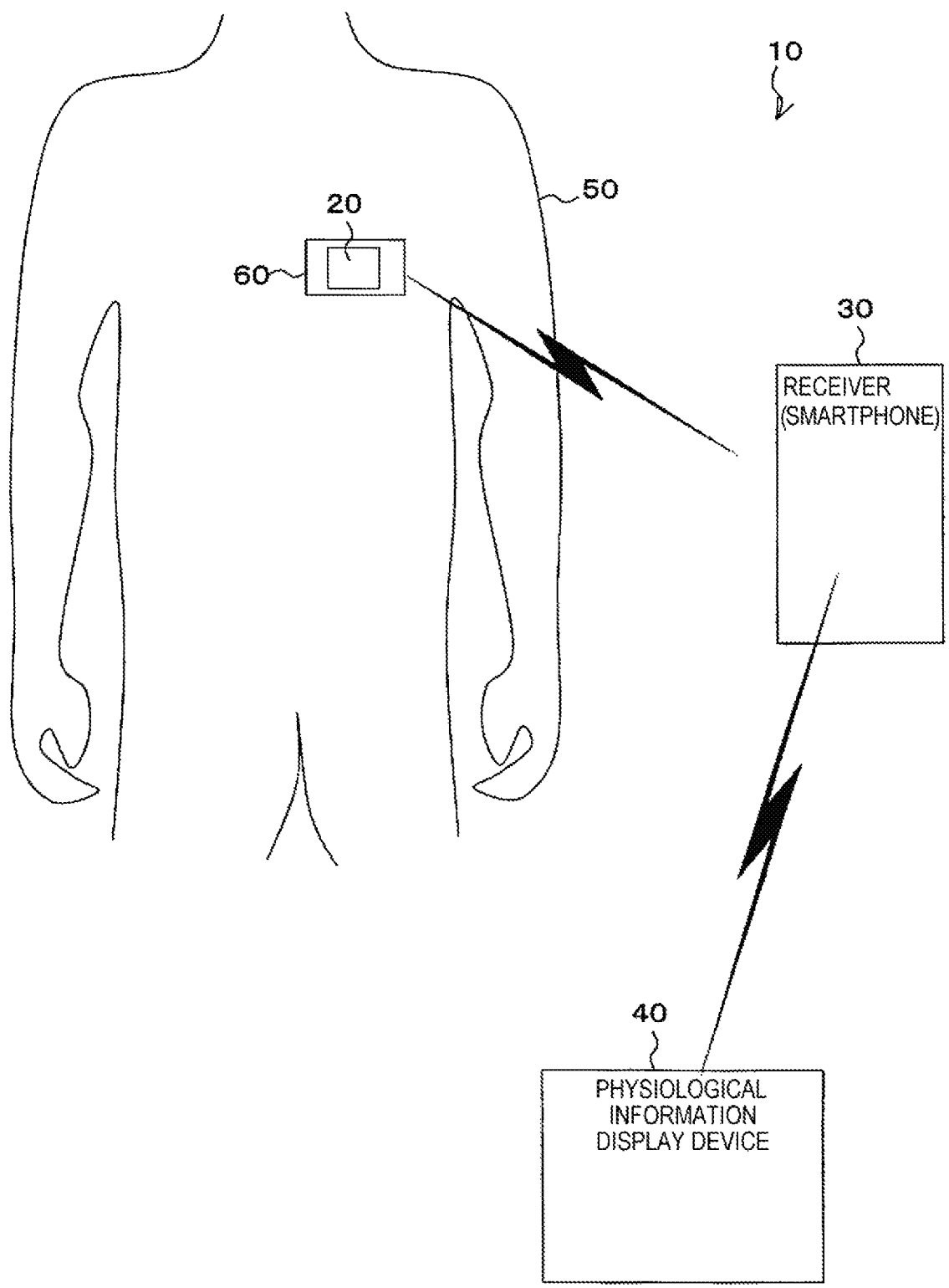
FIG. 1 is a schematic configuration diagram of a medical telemeter system 10.

In order to achieve the above object, an aspect of the present disclosure provides a physiological information detection sensor including: a plurality of first substrates arranged in multiple tiers; a second substrate; a first connecting portion that electrically connects adjacent first substrates to each other among the plurality of first substrates; and an insulating member. Each of the plurality of first substrates has a defibrillation protection resistor mounted thereon and electrically connected to a physiological information detection unit. The second substrate has a circuit mounted thereon to process physiological information input from the physiological information detection unit via the defibrillation protection resistor. The insulating member is disposed between adjacent first substrates among the plurality of first substrates.

According to this aspect, it is possible to provide a physiological information detection sensor capable of implementing miniaturization while substantially ensuring a creepage distance and an air distance (e.g., implementing defibrillation protection).

This is implemented, firstly, by arranging the plurality of first substrates in multiple tiers to reduce the dimension of the physiological information detection sensor in a direction orthogonal to the arrangement direction of the plurality of first substrates, compared to a case where the plurality of first substrates are not arranged in multiple tiers, and secondly, by disposing insulating members between adjacent first substrates among the plurality of first substrates and setting the air distance to substantially zero (0) (corresponding to the thickness of the insulating members) to reduce the dimension of the physiological information detection sensor in the arrangement direction of the plurality of first substrates.

Hereinafter, a medical telemeter system 10, which is an exemplary embodiment of the present disclosure, will be described with reference to the attached drawings. In each drawing, corresponding components are denoted by the same reference numerals, and redundant descriptions are omitted.

[Overview of Medical Telemeter System 10]

FIG. 1 is a schematic configuration diagram of the medical telemeter system 10.

As illustrated in FIG. 1, the medical telemeter system 10 includes a physiological information detection sensor 20, a receiver 30, and a physiological information display device 40 and the like.

The physiological information detection sensor 20 is attached to an electrode pad 60 affixed to the chest of a living body (hereinafter, referred to as a patient 50), measures the physiological information (in this embodiment, electrocardiogram) of the patient 50, and wirelessly transmits the measured electrocardiogram (electrocardiogram data) to the receiver 30.

The receiver 30 is, for example, a smartphone, receives the electrocardiogram wirelessly transmitted by the physiological information detection sensor 20, and displays the transmitted electrocardiogram on a display (not illustrated) provided in the receiver 30. Alternatively, the receiver 30 wirelessly transmits (transfers) the received electrocardiogram to the physiological information display device 40. Although a smartphone is exemplified as the receiver 30, it is not limited thereto as long as it can wirelessly receive a physiological signal from the physiological information detection sensor 20 and transmit the received physiological signal to the physiological information display device 40.

The physiological information display device 40 receives the electrocardiogram transmitted by the receiver 30 and displays the transmitted electrocardiogram on a display (not illustrated) provided in the physiological information display device 40.

[Physiological Information Detection Sensor]

Figure 2:
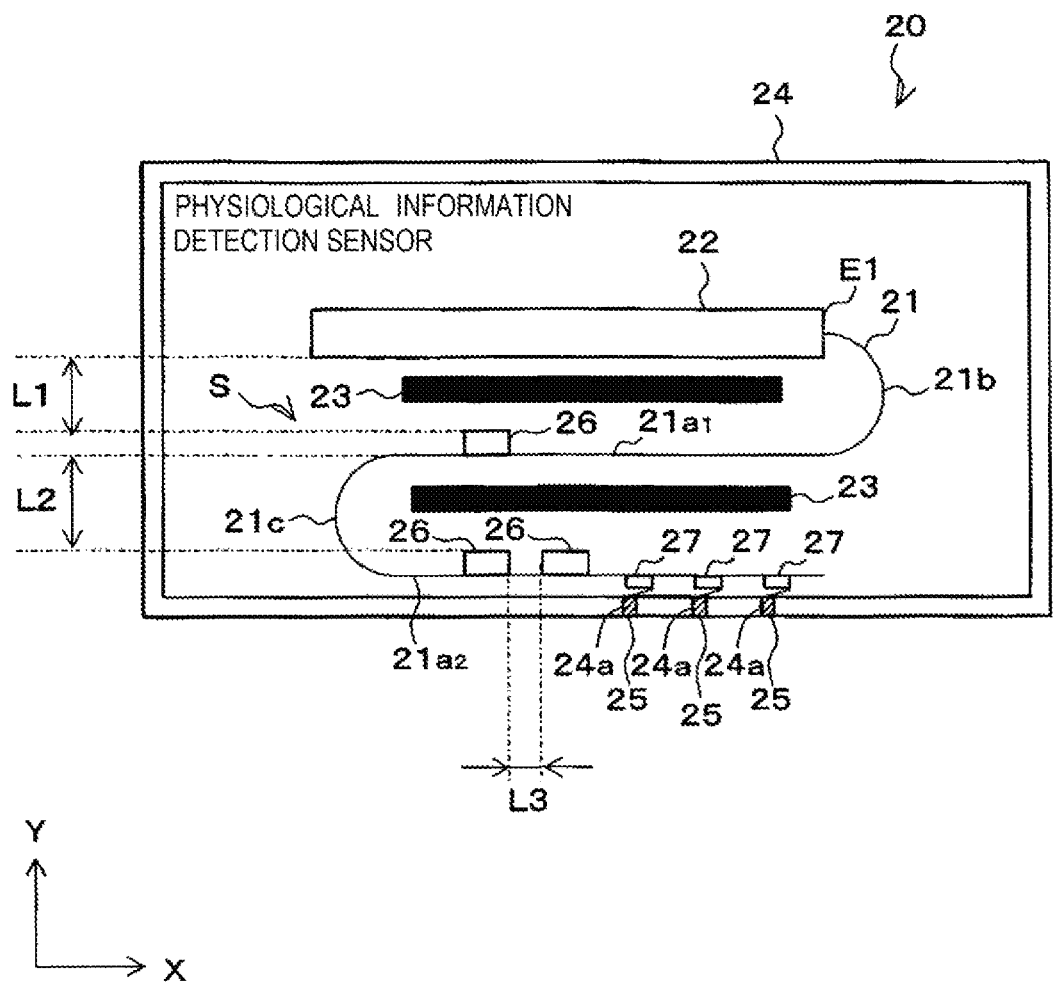
FIG. 2 is a schematic cross-sectional view of a physiological information detection sensor 20.
Figure 3:
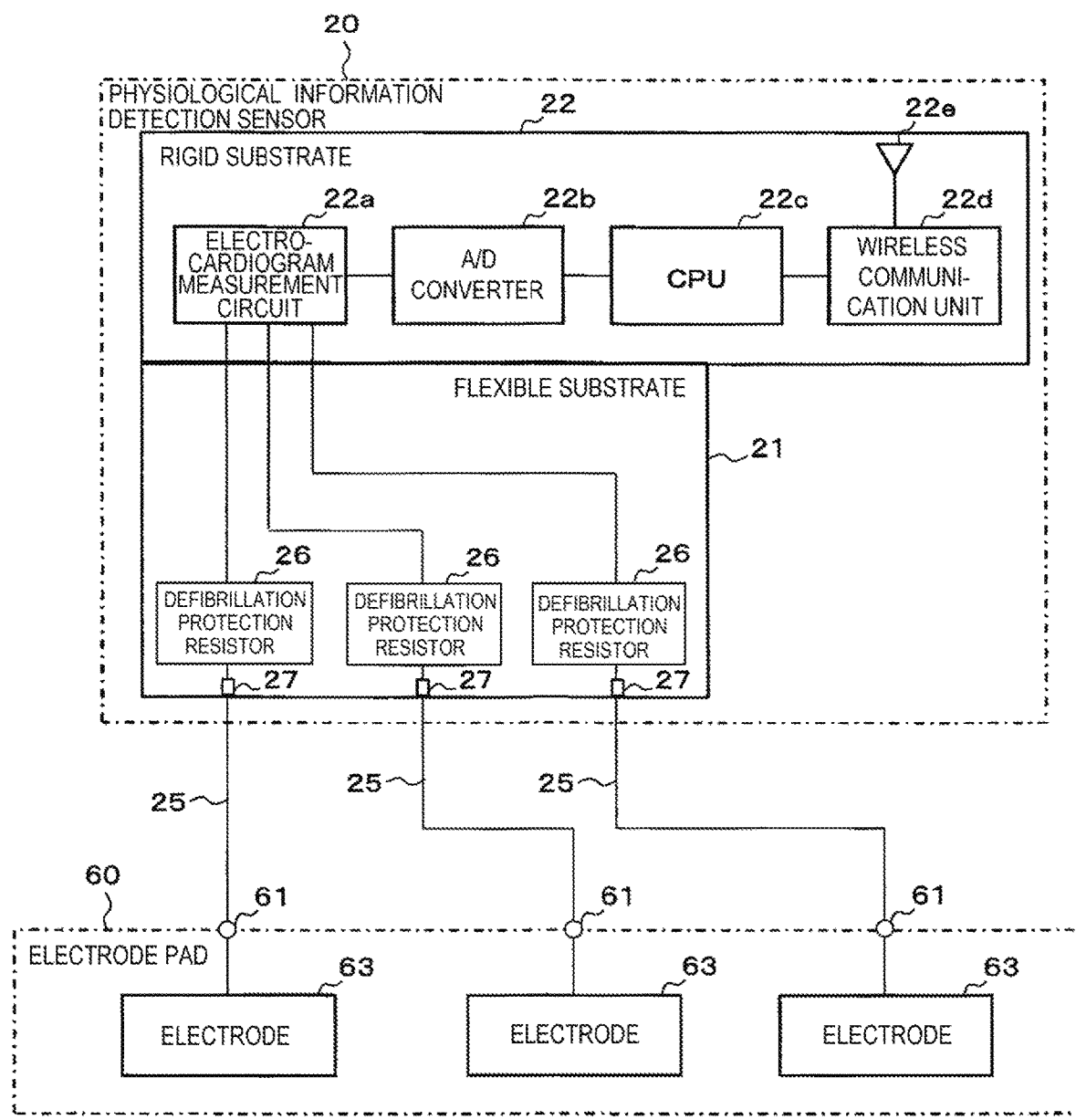

Next, the physiological information detection sensor 20 will be described. FIG. 2 is a schematic cross-sectional view of the physiological information detection sensor 20. FIG. 3 is a hardware configuration diagram of the physiological information detection sensor 20 and the like.

As illustrated in FIG. 2, the physiological information detection sensor 20 includes a flexible substrate 21, a rigid substrate 22, insulating members 23, and a casing 24 that accommodates these components.

The casing 24 is, for example, a rectangular box-shaped casing. The casing 24 is provided with three conductive portions 25 electrically connected to three contacts 61 (see FIGS. 3 and 5), respectively, which are provided on the electrode pad 60. Specifically, the three conductive portions 25 are fixed to the casing 24 in a state of being inserted into three through holes 24a, respectively, which are formed in the bottom portion of the casing 24 to which the electrode pad 60 is attached. The three through holes 24a penetrate the outer surface and the inner surface of the bottom portion of the casing 24.

Next, the rigid substrate 22 will be described.

As illustrated in FIG. 2, the rigid substrate 22 is accommodated in the casing 24 in a state of being fixed to the casing 24. Specifically, the rigid substrate 22 is fixed to the casing 24 by any known means such as a screw or an adhesive in a state where the rigid substrate 22 and the bottom portion of the casing 24 are parallel (or substantially parallel) to each other and a space S is formed therebetween such that the flexible substrate 21 is disposed in the space S. The rigid substrate 22 corresponds to the fourth substrate of the present disclosure.

As illustrated in FIG. 3, an electrocardiogram measurement circuit 22a, an A/D converter 22b, a CPU 22c, and a wireless communication unit 22d are mounted on the rigid substrate 22. The electrocardiogram measurement circuit 22a, the A/D converter 22b, the CPU 22c, and the wireless communication unit 22d correspond to the circuit of the present disclosure.

The electrocardiogram measurement circuit 22a is connected with three electrodes 63 provided on the electrode pad 60 via three defibrillation protection resistors 26, respectively. The electrocardiogram measurement circuit 22a amplifies signals input via the three defibrillation protection resistors 26 and outputs the signals as an electrocardiogram signal (ECG signal).

The A/D converter 22b samples the electrocardiogram signal (analog signal) input from the electrocardiogram measurement circuit 22a at a predetermined frequency and converts the signal into electrocardiogram data (digital value).

The CPU 22c executes a predetermined program to control various pieces of hardware (e.g., the wireless communication unit 22d) constituting the physiological information detection sensor 20. For example, the CPU 22c transmits the electrocardiogram converted by the A/D converter 22b (electrocardiogram data) to the receiver 30 via the wireless communication unit 22d.

The wireless communication unit 22d is, for example, a communication module compatible with a Bluetooth low energy (BLE) technology (e.g., BLE module), and wirelessly communicates with another BLE-compatible device (e.g., the receiver 30) within a short distance (e.g., 100 mm) via an antenna 22e.

Next, the flexible substrate 21 will be described.

Figure 4:
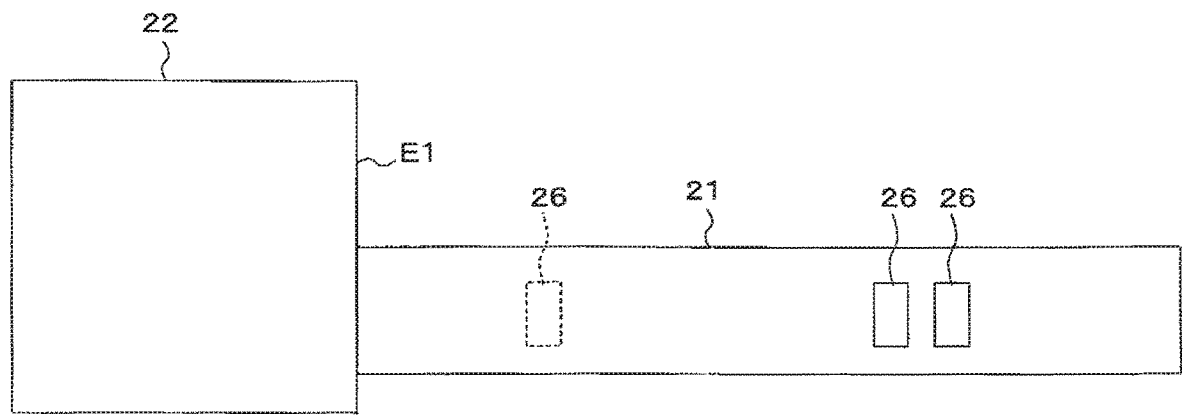
FIG. 4 is a plan view for explaining a relationship between a flexible substrate 21 and a rigid substrate 22.

FIG. 4 is a plan view for explaining the relationship between the flexible substrate 21 and the rigid substrate 22.

As illustrated in FIG. 4, the flexible substrate 21 is partially fixed to the rigid substrate 22 and extends from a side E1 of the rigid substrate 22 in a direction perpendicular (or substantially perpendicular) to the side E1.

As illustrated in FIG. 2, the flexible substrate 21 is folded twice in a bellows shape toward the rigid substrate 22 side, and is sandwiched between the rigid substrate 22 and the bottom portion of the casing 24 in a state where a first substrate portion $21a_1$, a second substrate portion $21a_2$, and the rigid substrate 22 are arranged in multiple tiers. At this time, the flexible substrate 21 is sandwiched between the rigid substrate 22 and the bottom portion of the casing 24 such that an air distance L1 between the first substrate portion $21a_1$ and the rigid substrate 22 and an air distance L2 between the first substrate portion $21a_1$ and the second substrate portion $21a_2$ become substantially zero (0) (corresponding to the thickness of the insulating members 23). The first substrate portion $21a_1$ and the second substrate portion $21a_2$ correspond to the third substrate of the present disclosure, and the rigid substrate 22 corresponds to the fourth substrate of the present disclosure.

As described above, when the flexible substrate 21 is folded in a bellows shape such that the first substrate portion $21a_1$, the second substrate portion $21a_2$, and the rigid substrate 22 are arranged in multiple tiers, it is possible to reduce the dimension of the physiological information detection sensor 20 in the X direction in FIG. 2, compared to the case where the flexible substrate 21 is not folded (see, e.g., FIG. 4).

As illustrated in FIG. 2, three spring contacts 27 mounted on the second substrate portion $21a_2$ are electrically connected to the three conductive portions 25 provided in the casing 24, respective, in a state where the flexible substrate 21 is sandwiched between the rigid substrate 22 and the bottom portion of the casing 24. Further, the sheet-like insulating members 23 such as high-voltage resistant sheets (not illustrated) wound around the flexible substrate 21 in a state of covering the respective defibrillation protection resistors 26 mounted on the first substrate portion $21a_1$ and the second substrate portion $21a_2$, are disposed between the first substrate portion $21a_1$ and the rigid substrate 22 and between the first substrate portion $21a_1$ and the second substrate portion $21a_2$.

Therefore, when the insulating members 23 are disposed between the first substrate portion $21a_1$ and the rigid substrate 22 and between the first substrate portion $21a_1$ and the second substrate portion $21a_2$, the first substrate portion $21a_1$ and the rigid substrate 22, and the first substrate portion $21a_1$ and the second substrate portion $21a_2$ may be insulated from each other even though the air distances L1 and L2 are set to substantially zero (0) (corresponding to the thickness of the insulating members 23). As a result, when the air distances L1 and L2 are set (e.g., a total of 8 mm of L1=4 mm and L2=4 mm), the dimension of the physiological information detection sensor 20 in the Y direction in FIG. 2 may be reduced, compared to the case of insulation between the first substrate portion $21a_1$ and the rigid substrate 22 and between the first substrate portion $21a_1$ and the second substrate portion $21a_2$.

The first substrate portion $21a_1$ and the rigid substrate 22 are electrically connected by a first bent portion 21b. The first substrate portion $21a_1$ and the second substrate portion $21a_2$ are electrically connected by a second bent portion 21c. The first bent portion 21b corresponds to the second connecting portion of the present disclosure, and the second bent portion 21c corresponds to the third connecting portion of the present disclosure.

In a portion of the flexible substrate 21, the first substrate portion $21a_1$, the second substrate portion $21a_2$, the first bent portion 21b, and the second bent portion 21c are formed by folding the flexible substrate 21 twice toward the rigid substrate 22 side in a bellows shape.

On the flexible substrate 21, the three defibrillation protection resistors 26 are mounted corresponding to the three electrodes 63 provided on the electrode pad 60. Specifically, the first substrate portion $21a_1$ is mounted with one defibrillation protection resistor 26 and the second substrate portion $21a_2$ is mounted with two defibrillation protection resistors 26. The first substrate portion $21a_1$ may be mounted with two defibrillation protection resistors 26 and the second substrate portion $21a_2$ may be mounted with one defibrillation protection resistor 26. The defibrillation protection resistor 26 is mounted while maintaining at least a creepage distance L3 (see FIG. 2; e.g., 4 mm).

Further, the three spring contacts 27 are mounted on the flexible substrate 21 (the second substrate portion $21a_2$) so as to be electrically connected to the three conductive portions 25 provided in the casing 24, respectively. As illustrated in FIG. 3, the three spring contacts 27 are electrically connected to the three defibrillation protection resistors 26, respectively, by wiring patterns or the like. Further, the three defibrillation protection resistors 26 are electrically connected to the electrocardiogram measurement circuit 22a mounted on the rigid substrate 22, respectively, by wiring patterns or the like.

[Electrode Pad]

Figure 5:
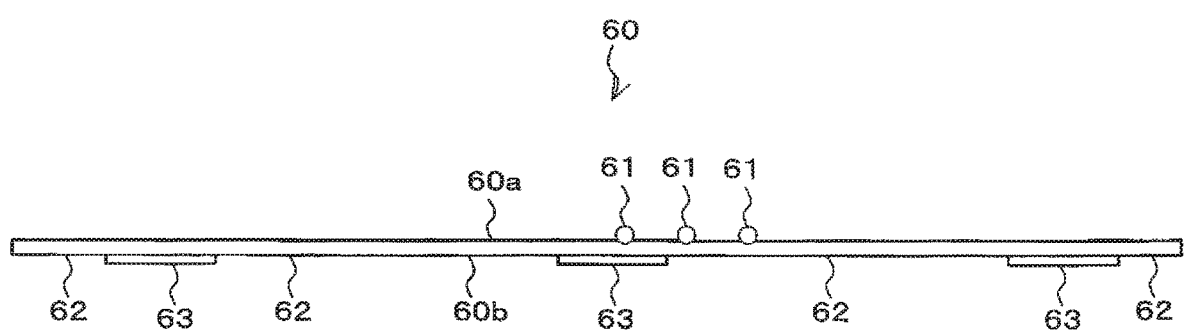
FIG. 5 is a schematic cross-sectional view of an electrode pad 60.
Figure 6:
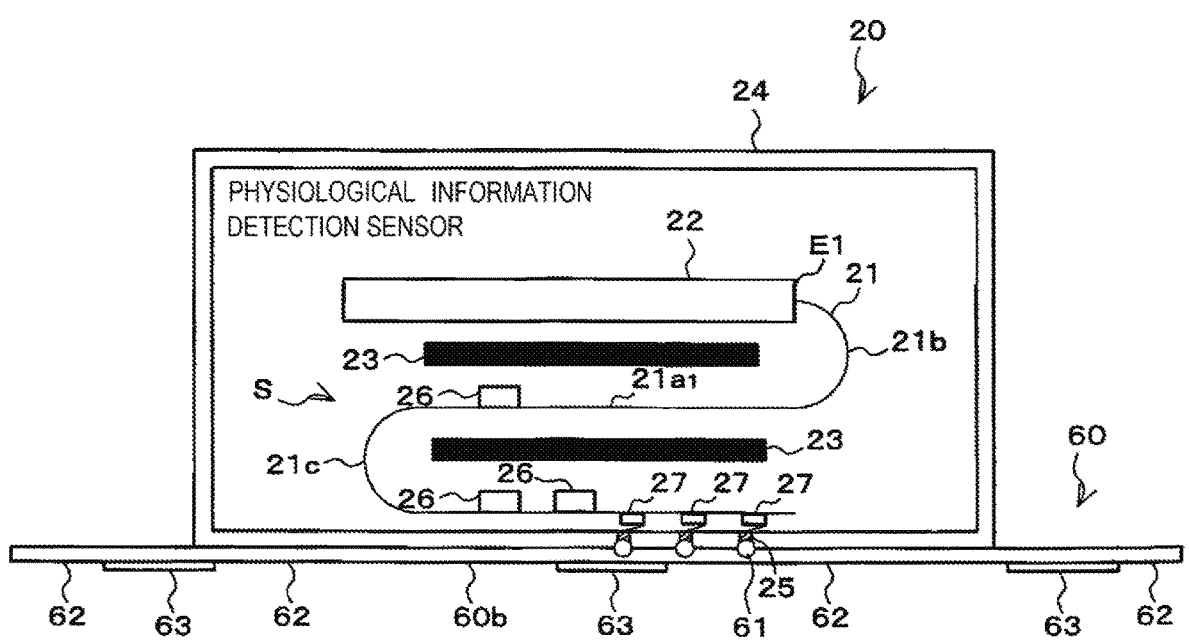
FIG. 6 is a schematic cross-sectional view of the electrode pad 60 to which the physiological information detection sensor 20 is attached.

Next, the electrode pad 60 will be described. FIG. 5 is a schematic cross-sectional view of the electrode pad 60. FIG. 6 is a schematic cross-sectional view of the electrode pad 60 to which the physiological information detection sensor 20 is attached.

As illustrated in FIG. 5, the electrode pad 60 includes a surface on the side where the physiological information detection sensor 20 (the casing 24) is mounted (hereinafter, referred to as a sensor mounting surface 60a) and a surface opposite thereto (hereinafter, referred to as an adhesive surface 60b).

The sensor mounting surface 60a is provided with the three contacts 61, each of which is electrically connected to one of the three conductive portions 25 of the physiological information detection sensor 20 mounted on the sensor mounting surface 60a. As illustrated in FIG. 6, the physiological information detection sensor 20 is detachably mounted on the electrode pad 60 (the sensor mounting surface 60a) by any known means in a state where the three conductive portions 25 and the three contacts 61 are electrically connected to each other.

The adhesive surface 60b is provided with an adhesive portion 62 and three electrodes 63 (three lead electrodes R, L, and F). By the action of the adhesive portion 62, the physiological information detection sensor 20 (and the electrode pad 60 on which the physiological information detection sensor 20 is mounted) is attached to the chest of the patient 50 in a state where the three electrodes 63 are brought into contact with the chest of the patient 50. As illustrated in FIG. 3, the three electrodes 63 are electrically connected to the three contacts 61, respectively, by wiring patterns or the like.

As described above, according to the present exemplary embodiment, it is possible to provide the physiological information detection sensor 20 capable of implementing miniaturization (miniaturization in the X and Y directions in FIG. 2) while substantially ensuring a creepage distance and an air distance (e.g., implementing defibrillation protection).

This is implemented, firstly, by arranging the plurality of first substrates (the first substrate portion $21a_1$ and the second substrate portion $21a_2$) in multiple tiers to reduce the dimension of the physiological information detection sensor 20 in a direction orthogonal to the arrangement direction of the plurality of first substrates (the X direction in FIG. 2), compared to a case where the plurality of first substrates are not arranged in multiple tiers, and secondly, by disposing the insulating members 23 between the first substrate portion $21a_1$ and the rigid substrate 22 and between the first substrate portion $21a_1$ and the second substrate portion $21a_2$ and setting the air distances (L1 and L2) to substantially zero (0) (corresponding to the thickness of the insulating members) to reduce the dimension of the physiological information detection sensor 20 in the arrangement direction (the Y direction in FIG. 2) of the plurality of first substrates (the first substrate portion $21a_1$ and the second substrate portion $21a_2$).

Specifically, according to the present exemplary embodiment, the following effects may be obtained.

First, when the flexible substrate 21 is folded in a bellows shape such that the first substrate portion $21a_1$, the second substrate portion $21a_2$, and the rigid substrate 22 are arranged in multiple tiers, it is possible to reduce the dimension of the physiological information detection sensor 20 in the X direction in FIG. 2, compared to the case where the flexible substrate 21 is not folded (see, e.g., FIG. 4).

Second, when the insulating members 23 are disposed between the first substrate portion $21a_1$ and the rigid substrate 22 and between the first substrate portion $21a_1$ and the second substrate portion $21a_2$, the first substrate portion $21a_1$ and the rigid substrate 22, and the first substrate portion $21a_1$ and the second substrate portion $21a_2$ may be insulated from each other even though the air distances L1 and L2 are set to substantially zero (0) (corresponding to the thickness of the insulating members 23). As a result, when the air distances L1 and L2 are set (e.g., a total of 8 mm of L1=4 mm and L2=4 mm), the dimension of the physiological information detection sensor 20 in the Y direction in FIG. 2 may be reduced, compared to the case of insulation between the first substrate portion $21a_1$ and the rigid substrate 22 and between the first substrate portion $21a_1$ and the second substrate portion $21a_2$.

Next, a modification will be described.

First, a modification of the flexible substrate 21 will be described. FIG. 7 is a view for explaining a modification of the flexible substrate 21. In FIG. 7, the casing 24, the spring contacts 27, and the like are omitted.

As illustrated in FIG. 7, a flexible substrate 21A of the modification is folded once toward the rigid substrate 22 side, and is sandwiched between the rigid substrate 22 and the bottom portion of the casing 24 in a state where the first substrate portion $21a_1$ and the rigid substrate 22 are arranged in multiple tiers. At this time, the flexible substrate 21A is sandwiched between the rigid substrate 22 and the bottom portion of the casing 24 such that the air distance L1 between the first substrate portion $21a_1$ and the rigid substrate 22 become substantially zero (0) (corresponding to the thickness of the insulating member 23). The three defibrillation protection resistors 26 are mounted on the first substrate portion $21a_1$.

The modification may also exhibit the same effects as those of the above exemplary embodiment.

Next, another modification of the flexible substrate 21 will be described. FIG. 8 is a view for explaining another modification of the flexible substrate 21. In FIG. 8, the casing 24, the spring contacts 27, and the like are omitted.

As illustrated in FIG. 8, a flexible substrate 21B of the modification is folded three times toward the rigid substrate 22 side, and is sandwiched between the rigid substrate 22 and the bottom portion of the casing 24 in a state where the first substrate portion $21a_1$, the second substrate portion $21a_2$, a third substrate portion $21a_3$, and the rigid substrate 22 are arranged in multiple tiers. At this time, the flexible substrate 21B is sandwiched between the rigid substrate 22 and the bottom portion of the casing 24 such that the air distance L1 between the first substrate portion $21a_1$ and the rigid substrate 22 and the air distance L2 between the first substrate portion $21a_1$ and the second substrate portion $21a_2$ (and further, an air distance L4 between the second substrate portion $21a_2$ and the third substrate portion $21a_3$) become substantially zero (0) (corresponding to the thickness of the insulating members 23). Each of the first to third substrate portions $21a_1$ to $21a_3$ is mounted with one defibrillation protection resistor 26.

The modification may also exhibit the same effects as those of the above exemplary embodiment.

Figure 9:
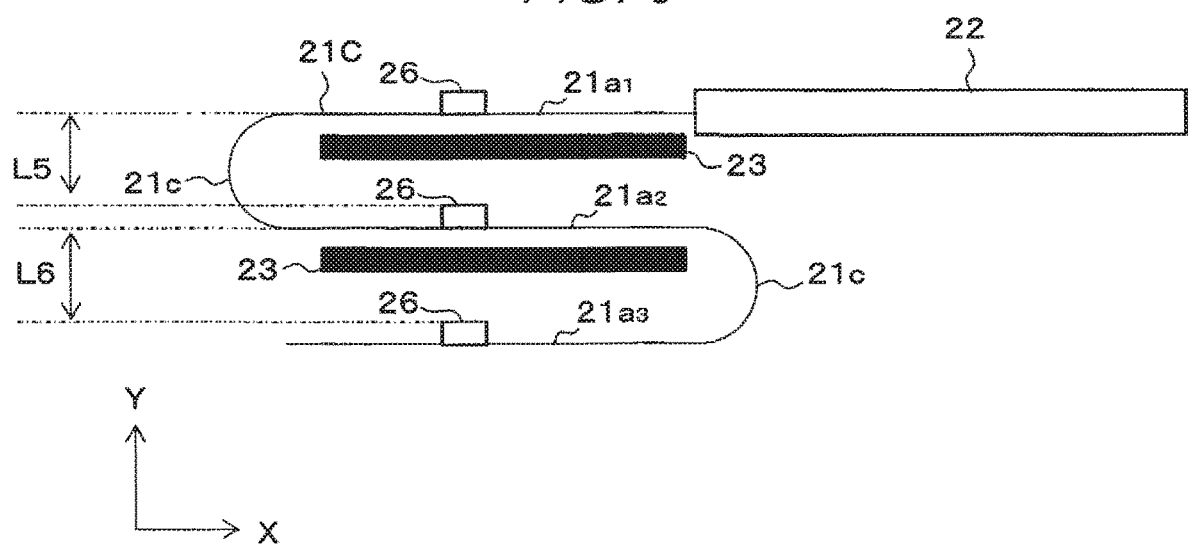
FIG. 9 is a view for explaining still another modification of the flexible substrate 21.

Next, still another modification of the flexible substrate 21 will be described. FIG. 9 is a view for explaining still another modification of the flexible substrate 21. In FIG. 9, the casing 24, the spring contacts 27, and the like are omitted.

As illustrated in FIG. 9, a flexible substrate 21C of the modification is folded twice in a bellows shape, and is disposed at a position adjacent to the rigid substrate 22 in a state where the first substrate portion $21a_1$, the second substrate portion $21a_2$, and the third substrate portion $21a_3$ are arranged in multiple tiers. At this time, the flexible substrate 21C is held by a predetermined means such that an air distance L5 between the first substrate portion $21a_1$ and the second substrate portion $21a_2$ and an air distance L6 between the second substrate portion $21a_2$ and the third substrate portion $21a_3$ become substantially zero (0) (corresponding to the thickness of the insulating members 23). Each of the first to third substrate portions $21a_1$ to $21a_3$ is mounted with one defibrillation protection resistor 26. In FIG. 9, the first substrate portion $21a_1$, the second substrate portion $21a_2$, and the third substrate portion $21a3$ correspond to the plurality of first substrates of the present disclosure, and a second bent portion $21c$ corresponds to the first connecting portion of the present disclosure.

The modification may also exhibit the same effects as those of the above exemplary embodiment. That is, it is possible to provide a physiological information detection sensor capable of implementing miniaturization while substantially ensuring a creepage distance and an air distance (e.g., implementing defibrillation protection).

This is implemented, firstly, by arranging the plurality of first substrates (the first substrate portion $21a_1$, the second substrate portion $21a_2$, and the third substrate portion $21a_3$) in multiple tiers to reduce the dimension of the physiological information detection sensor 20 in a direction orthogonal to the arrangement direction of the plurality of first substrates (the X direction in FIG. 9), compared to a case where the plurality of first substrates are not arranged in multiple tiers, and secondly, by disposing the insulating members 23 between adjacent first substrates among the plurality of first substrates (between the first substrate portion $21a_1$ and the second substrate portion $21a_2$ and between the second substrate portion $21a_2$ and the third substrate portion $21a_3$) and setting the air distances L5 and L6 to substantially zero (0) (corresponding to the thickness of the insulating members 23) to reduce the dimension of the physiological information detection sensor 20 in the arrangement direction (the Y direction in FIG. 9) of the plurality of first substrates.

Figure 10:
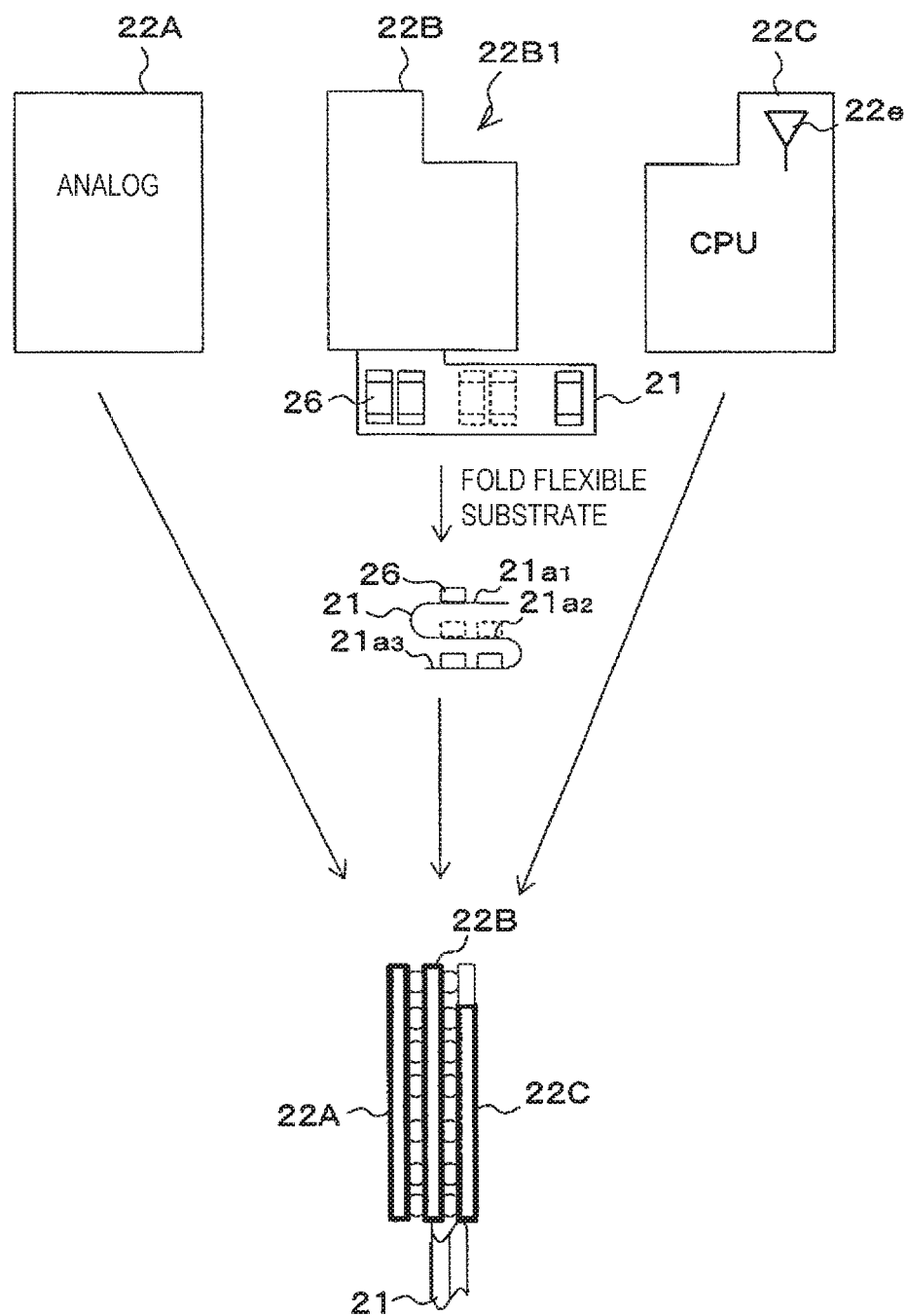
FIG. 10 is a view for explaining a modification of the rigid substrate 22.

Next, a modification of the rigid substrate 22 will be described. FIG. 10 is a view for explaining a modification of the rigid substrate 22. In FIG. 10, the casing 24, the spring contacts 27, and the like are omitted.

As illustrated in FIG. 10, the rigid substrate 22 of the modification includes three rigid substrates arranged in multiple tiers, specifically, a first rigid substrate 22A mounted with an analog circuit, a second rigid substrate 22B mounted with an input unit to which physiological information is input from the electrode 63 via the defibrillation protection resistor 26, and a third rigid substrate 22C mounted with a digital circuit.

The second rigid substrate 22B is provided with a notch 22B1 at a position corresponding to the antenna $22e$ mounted on the third rigid substrate 22C in order to suppress radio waves from the antenna $22e$ from being blocked.

The flexible substrate 21 is partially fixed to the second rigid substrate 22B, and extends from one side of the second rigid substrate 22B in a direction parallel (or substantially parallel) to the one side.

Further, the flexible substrate 21 is folded twice in a bellows shape, and is disposed at a position adjacent to the rigid substrate 22 (22A to 22C) in a state where the first substrate portion $21a_1$, the second substrate portion $21a_2$, and the third substrate portion $21a_3$ are arranged in multiple tiers.

The first substrate portion $21a_1$ is mounted with one defibrillation protection resistor 26, the second substrate portion $21a_2$ is mounted with two defibrillation protection resistors 26, and the third substrate portion $21a_3$ is mounted with two defibrillation protection resistors 26. In the modification, in addition to the three defibrillation protection resistors 26 described in the above exemplary embodiment, two defibrillation protection resistors 26 are added for impedance breathing. Even in the above exemplary embodiment, two defibrillation protection resistors 26 may be added for impedance breathing.

The modification may also exhibit the same effects as those of the above exemplary embodiment.

Figure 11:
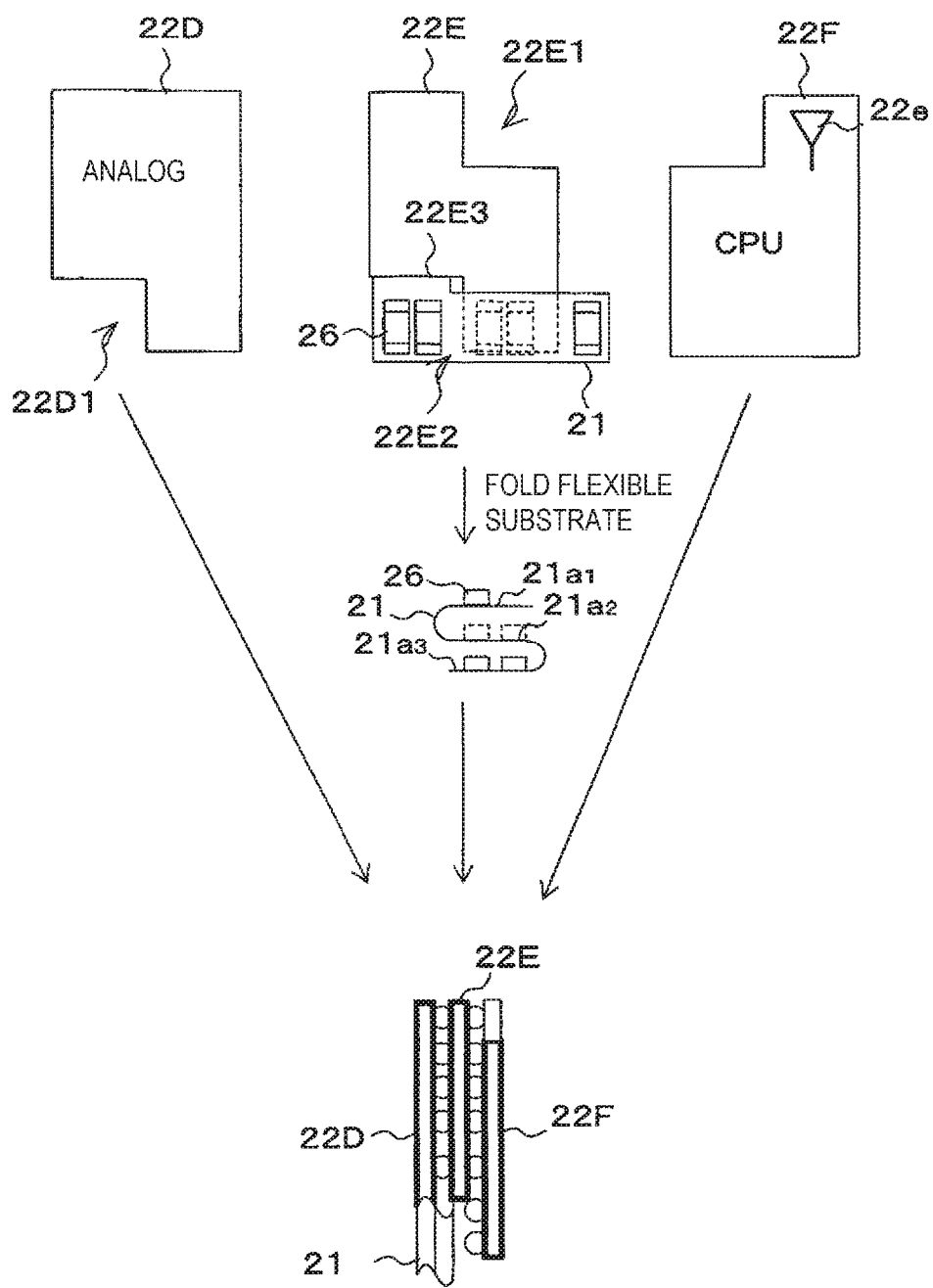
FIG. 11 is a view for explaining another modification of the rigid substrate 22.

Next, another modification of the rigid substrate 22 will be described. FIG. 11 is a view for explaining another modification of the rigid substrate 22. In FIG. 11, the casing 24, the spring contacts 27, and the like are omitted.

As illustrated in FIG. 11, the rigid substrate 22 of the modification includes three rigid substrates arranged in multiple tiers, specifically, a first rigid substrate 22D mounted with an analog circuit, a second rigid substrate 22E mounted with an input unit to which physiological information is input from the electrode 63 via the defibrillation protection resistor 26, and a third rigid substrate 22F mounted with a digital circuit.

The second rigid substrate 22E is provided with a notch 22E1 at a position corresponding to the antenna $22e$ mounted on the third rigid substrate 22F in order to suppress radio waves from the antenna $22e$ from being blocked.

Further, the second rigid substrate 22E is provided with a notch 22E2 at a position diagonal to the notch 22E1.

Further, the first rigid substrate 22D is provided with a notch 22D1 at a position corresponding to the notch 22E2 provided in the second rigid substrate 22E. Therefore, the notch 22D1 provided in the first rigid substrate 22D and the notch 22E2 provided in the second rigid substrate 22E overlap each other to form an installation space for the flexible substrate 21.

The flexible substrate 21 is partially fixed to the second rigid substrate 22E, and extends from one side of the second rigid substrate 22E (a side 22E3 constituting the notch 22E2) in a direction parallel (or substantially parallel) to the side 22E3.

Further, the flexible substrate 21 is folded twice in a bellows shape, and is disposed in the installation space for the flexible substrate 21 in a state where the first substrate portion $21a_1$, the second substrate portion $21a_2$, and the third substrate portion $21a_3$ are arranged in multiple tiers.

The first substrate portion $21a_1$ is mounted with one defibrillation protection resistor 26, the second substrate portion $21a_2$ is mounted with two defibrillation protection resistors 26, and the third substrate portion $21a_3$ is mounted with two defibrillation protection resistors 26. In the modification, in addition to the three defibrillation protection resistors 26 described in the above exemplary embodiment, two defibrillation protection resistors 26 are added for impedance breathing.

The modification may also exhibit the same effects as those of the above exemplary embodiment.

Figure 12:
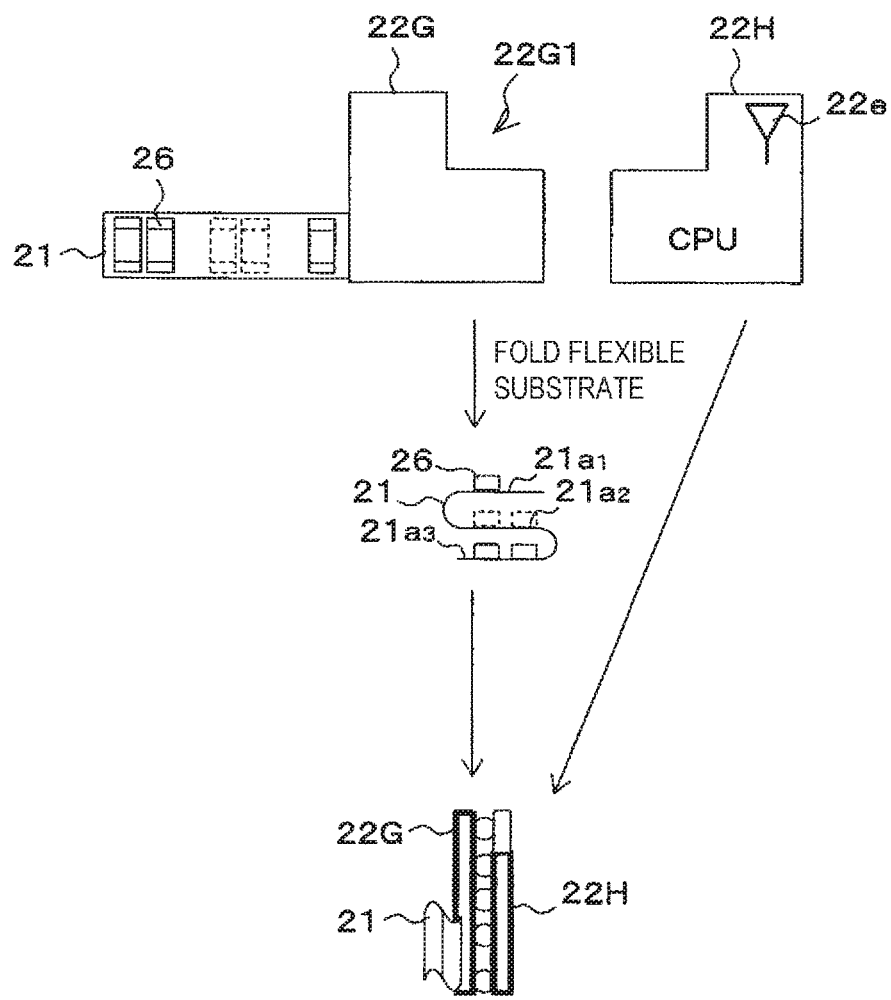
FIG. 12 is a view for explaining still another modification of the rigid substrate 22.

Next, still another modification of the rigid substrate 22 will be described. FIG. 12 is a view for explaining still another modification of the rigid substrate 22. In FIG. 12, the casing 24, the spring contacts 27, and the like are omitted.

As illustrated in FIG. 12, the rigid substrate 22 of the modification includes two rigid substrates arranged in multiple tiers, specifically, a first rigid substrate 22G mounted with an input unit to which physiological information is input from the electrode 63 via the defibrillation protection resistor 26, and a second rigid substrate 22H mounted with an analog circuit and a digital circuit.

The second rigid substrate 22G is provided with a notch 22G1 at a position corresponding to the antenna 22e mounted on the second rigid substrate 22H in order to suppress radio waves from the antenna 22e from being blocked.

The flexible substrate 21 is partially fixed to the first rigid substrate 22G, and extends from one side of the first rigid substrate 22G in a direction perpendicular (or substantially perpendicular) to the one side.

Further, the flexible substrate 21 is folded twice in a bellows shape, and is disposed at a position adjacent to the rigid substrate 22 (22G to 22H) in a state where the first substrate portion $21a_1$, the second substrate portion $21a_2$, and the third substrate portion $21a_3$ are arranged in multiple tiers.

The first substrate portion $21a_1$ is mounted with one defibrillation protection resistor 26, the second substrate portion $21a_2$ is mounted with two defibrillation protection resistors 26, and the third substrate portion $21a_3$ is mounted with two defibrillation protection resistors 26. In the modification, in addition to the three defibrillation protection resistors 26 described in the above exemplary embodiment, two defibrillation protection resistors 26 are added for impedance breathing.

The modification may also exhibit the same effects as those of the above exemplary embodiment.

In the above-described exemplary embodiments, descriptions have been made on an example in which a part of the flexible substrate 21 is used as the bent portion 21c serving as the first connecting portion or the third connecting portion, and as the bent portion 21b serving as the second connecting portion. However, the present disclosure is not limited thereto. For example, a wiring such as a lead wire or a jumper wire may be used in place of the bent portion 21c and the bent portion 21b. In this case, a rigid substrate may be used as the first substrate portion $21a_1$, the second substrate portion $21a_2$, and the third substrate portion $21a_3$ in place of the flexible substrate 21.

Further, in the above-described exemplary embodiments, descriptions have been made on an example in which the high-voltage resistant sheet wound around the flexible substrate 21 is used as the insulating member 23. However, the present disclosure is not limited thereto. For example, an insulating vinyl tape or an insulating solid (e.g., an insulating board or an insulating plate) may be used.

Further, in the above-described exemplary embodiments, descriptions have been made on an example in which the spring contact 27 is used as a contact to which the defibrillation protection resistor 26 is electrically connected and which is electrically connected to the contact 61 provided on the electrode pad 60. However, the present disclosure is not limited thereto. For example, an ordinary contact other than the spring contact 27 may be used as a contact electrically connected to the defibrillation protection resistor 26 and electrically connected to the contact 61 provided on the electrode pad 60. Further, the defibrillation protection resistor 26 and the conductive portion 25 may be electrically connected by using a wiring such as a lead wire or the like without using the spring contact 27.

All the numerical values described in the above-described exemplary embodiments are illustrative, and it is clear that appropriate numerical values different from those may be used.

The above-described exemplary embodiments are merely illustrative in all respects. The present disclosure is not to be interpreted restrictively by the description of the above-described exemplary embodiments. The present disclosure may be embodied in various other forms without departing from its spirit or main characteristics.

What is claimed is:

1. A physiological information detection sensor comprising:
    a plurality of first substrates arranged in multiple tiers;
    a second substrate;
    a first connecting portion that electrically connects adjacent first substrates to each other among the plurality of first substrates; and
    an insulating member,
    wherein each of the plurality of first substrates has a defibrillation protection resistor mounted thereon and electrically connected to a physiological information detection unit,
    the second substrate has a circuit mounted thereon and is configured to process physiological information input from the physiological information detection unit via the defibrillation protection resistor, and
    the insulating member is disposed between adjacent first substrates among the plurality of first substrates.

2. The physiological information detection sensor according to claim 1, wherein the plurality of first substrates and the first connecting portion are configured by folding a flexible substrate, a part of which is fixed to the second substrate, at least once.

3. The physiological information detection sensor according to claim 2, wherein the plurality of first substrates are arranged in multiple tiers in a state where adjacent substrates face each other.

4. The physiological information detection sensor according to claim 1, wherein the plurality of first substrates are arranged in multiple tiers in a state where adjacent substrates face each other.

5. A physiological information detection sensor comprising:
   a third substrate and a fourth substrate that are arranged in multiple tiers;
   a second connecting portion that electrically connects the third substrate and the fourth substrate to each other; and
   an insulating member,
   wherein the third substrate has a defibrillation protection resistor mounted thereon and electrically connected to a physiological information detection unit,
   the fourth substrate has a circuit mounted thereon and configured to process physiological information input from the physiological information detection unit via the defibrillation protection resistor, and
   the insulating member is disposed between the third substrate and the fourth substrate.

6. The physiological information detection sensor according to claim 5, wherein the third substrate and the second connecting portion are configured by folding a flexible substrate, a part of which is fixed to the fourth substrate, toward the fourth substrate.

7. The physiological information detection sensor according to claim 6, wherein the third substrate and the fourth substrate are arranged in multiple tiers in a state of facing each other.

8. The physiological information detection sensor according to claim 5, wherein the third substrate and the fourth substrate are arranged in multiple tiers in a state of facing each other.

9. The physiological information detection sensor according to claim 5, further comprising:
   a plurality of the third substrates; and
   a third connecting portion that electrically connects adjacent third substrates to each other among the plurality of third substrates,
   wherein the insulating member is disposed between the third substrate and the fourth substrate and between the third substrates disposed adjacent to each other among the plurality of third substrates.

10. The physiological information detection sensor according to claim 9, wherein the plurality of third substrates, the second connecting portion, and the third connecting portion are configured by folding a flexible substrate, a part of which is fixed to the fourth substrate, at least twice toward the fourth substrate.

11. The physiological information detection sensor according to claim 10, wherein the plurality of third substrates are arranged in multiple tiers in a state where adjacent substrates face each other.

12. The physiological information detection sensor according to claim 11, wherein the insulating member is a sheet-like insulating member wound around the flexible substrate in a state of covering the defibrillation protection resistor.

13. The physiological information detection sensor according to claim 10, further comprising:
   a casing that accommodates the fourth substrate, the flexible substrate, and the insulating member,
   wherein the fourth substrate is accommodated in the casing in a state of being fixed to the casing, and
   the flexible substrate is accommodated in the casing in a state of being sandwiched between the fourth substrate and the casing.

14. The physiological information detection sensor according to claim 13, wherein the casing includes a conductive portion to which the physiological information detection unit is electrically connected,
   the flexible substrate has a spring contact mounted thereon and electrically connected to the conductive portion, and
   the flexible substrate is accommodated in the casing in a state of being sandwiched between the fourth substrate and the casing such that the spring contact is electrically connected to the conductive portion of the casing.

15. The physiological information detection sensor according to claim 14, wherein the insulating member is a sheet-like insulating member wound around the flexible substrate in a state of covering the defibrillation protection resistor.

16. The physiological information detection sensor according to claim 13, wherein the insulating member is a sheet-like insulating member wound around the flexible substrate in a state of covering the defibrillation protection resistor.

17. The physiological information detection sensor according to claim 10, wherein the insulating member is a sheet-like insulating member wound around the flexible substrate in a state of covering the defibrillation protection resistor.

18. The physiological information detection sensor according to claim 9, wherein the plurality of third substrates are arranged in multiple tiers in a state where adjacent substrates face each other.

19. The physiological information detection sensor according to claim 18, wherein the insulating member is a sheet-like insulating member wound around the flexible substrate in a state of covering the defibrillation protection resistor.

* * * * *